(12) United States Patent
Leem et al.

(10) Patent No.: US 11,083,385 B2
(45) Date of Patent: Aug. 10, 2021

(54) APPARATUS FOR MEASURING BLOOD CIRCULATION DISORDERS, AND METHOD THEREFOR

(71) Applicant: UNIVERSITY OF ULSAN FOUNDATION FOR INDUSTRY COOPERATION, Ulsan (KR)

(72) Inventors: Chae Hun Leem, Seoul (KR); Young Boum Lee, Incheon (KR); Moo Yong Rhee, Goyang-si (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 410 days.

(21) Appl. No.: 15/546,245

(22) PCT Filed: Aug. 25, 2015

(86) PCT No.: PCT/KR2015/008859
§ 371 (c)(1),
(2) Date: Jul. 25, 2017

(87) PCT Pub. No.: WO2016/133255
PCT Pub. Date: Aug. 25, 2016

(65) Prior Publication Data
US 2017/0367595 A1   Dec. 28, 2017

(30) Foreign Application Priority Data

Jan. 26, 2015  (KR) .................. 10-2015-0012097

(51) Int. Cl.
*A61B 5/0285* (2006.01)
*A61B 5/02* (2006.01)
*A61B 5/021* (2006.01)

(52) U.S. Cl.
CPC .............. *A61B 5/0285* (2013.01); *A61B 5/02* (2013.01); *A61B 5/021* (2013.01); *A61B 5/02007* (2013.01)

(58) Field of Classification Search
None
See application file for complete search history.

(56) References Cited

U.S. PATENT DOCUMENTS 4,784,152 A * 11/1988 Shinoda ................. A61B 5/021
                                                        600/503
5,099,853 A *  3/1992 Uemura ............. A61B 5/02116
                                                        600/492
(Continued)

FOREIGN PATENT DOCUMENTS

JP   2007-111244 A   5/2007
JP   2010-148690 A   7/2010
(Continued)

OTHER PUBLICATIONS

Foo, "Normality of Upper and Lower Peripheral Pulse Transit Time of Normotensive and Hypertensive Children", 2007, Journal of Clinical Monitoring and Computing, 21, 243-248 (Year: 2007).*
(Continued)

*Primary Examiner* — Jason M Sims
*Assistant Examiner* — James Stewart Stambaugh, III
(74) *Attorney, Agent, or Firm* — Novick, Kim & Lee, PLLC; Jae Youn Kim (57) ABSTRACT

The present invention relates to an apparatus for measuring blood circulation disorders, and a method therefor. The apparatus for measuring blood circulation disorders using a pulse wave transit time includes a measurement unit configured to measure a pulse wave and an electrocardiogram of a subject to be measured, a detection unit configured to detect time information of a peak value point of the electrocardiogram and a peak value point and a foot value point
(Continued)

of the pulse wave, an operation unit configured to calculate an average pulse wave transit time using the time information of the peak value point of the electrocardiogram and the peak value point and the foot value point of the pulse wave and calculate a blood circulation disorder determination index using the average pulse wave transit time, and a diagnosis unit configured to diagnose a blood circulation disorder using the blood circulation disorder determination index.

12 Claims, 6 Drawing Sheets

(56) References Cited

U.S. PATENT DOCUMENTS

| | | | | |
|---|---|---|---|---|
| 5,261,414 | A * | 11/1993 | Aung | A61B 5/02116 600/496 |
| 6,331,162 | B1 * | 12/2001 | Mitchell | A61B 5/02125 600/485 |
| 6,511,436 | B1 * | 1/2003 | Asmar | A61B 5/021 600/481 |
| 7,291,113 | B2 * | 11/2007 | Satoh | A61B 5/02116 600/500 |
| 9,510,761 | B2 * | 12/2016 | Areny | A61B 5/02125 |
| 9,526,444 | B2 * | 12/2016 | Kobayashi | A61B 5/02028 |
| 2005/0261593 | A1 * | 11/2005 | Zhang | A61B 5/021 600/485 |
| 2006/0211942 | A1 * | 9/2006 | Hoctor | A61B 5/02125 600/438 |
| 2006/0264771 | A1 * | 11/2006 | Lin | A61B 5/0402 600/513 |
| 2008/0027330 | A1 * | 1/2008 | Naghavi | A61B 5/0402 600/481 |
| 2008/0221461 | A1 * | 9/2008 | Zhou | A61B 5/021 600/485 |
| 2008/0262362 | A1 * | 10/2008 | Kolluri | A61B 5/02125 600/490 |
| 2010/0160794 | A1 * | 6/2010 | Banet | A61B 5/02125 600/485 |
| 2011/0275909 | A1 * | 11/2011 | Kim | A61B 5/02007 600/301 |
| 2014/0073969 | A1 * | 3/2014 | Zou | A61B 5/02108 600/479 |

FOREIGN PATENT DOCUMENTS

| | | |
|---|---|---|
| KR | 10-2008-0017525 A | 2/2008 |
| KR | 10-2013-0095664 A | 8/2013 |
| KR | 10-2014-0148074 A | 12/2014 |
| WO | 2014022906 A1 | 2/2014 |
| WO | 2014042845 A1 | 3/2014 |

OTHER PUBLICATIONS

Foo, "Pulse transit time ratio as a potential marker for paediatric crural and brachial blood pressure index", 2007, Journal of human hypertension, 21, 415-7 (Year: 2007).*

* cited by examiner

FIG. 1

Analysis result of disease group/normal group determination index A7
(1:disease group, 2:normal group)

FIG. 2A

Logistic regression analysis result of disease group/normal group determination index A7(In the case of setting 10% boundary region)

FIG. 2B

Analysis result of B1+B3 of cardiovascular disease group/cerebrovascular disease group determination index B4
(1:cardiovascular disease group, 2:cerebrovascular disease group)

FIG. 3A

Logistic regression analysis result of B1+B3 of cardiovascular disease group/cerebrovascular disease group determination index B4 (In the case of setting 10% boundary region)

APPARATUS FOR MEASURING BLOOD CIRCULATION DISORDERS, AND METHOD THEREFOR

TECHNICAL FIELD

The present invention relates to an apparatus for measuring blood circulation disorders using a pulse wave transit time, and a method therefor. More particularly, the present invention pertains to a blood circulation disorder measurement apparatus for measuring blood circulation disorders using a pulse wave transit time between pulse waves measured at different points or a transit time between a pulse wave and an electrocardiogram, and a method therefor.

BACKGROUND ART

Blood vessels are lifelines that supply nutrition to 60 trillion cells in our body. In order to maintain a human life, there is a need for a process in which the blood discharged by the beat of a heart is caused to flow to various parts of a body along an artery without clogging and are returned to the heart via a vein. As a result, oxygen and nutrients can be supplied to the respective tissues of the body, and the wastes consumed through metabolism can be removed. Thus, the health of the blood vessels is directly linked to our health. Serious diseases may be caused when inadvertently managing the blood vessels.

However, in recent years, our blood vessels are increasingly clogged due to westernized dietary habits, stress, obesity, lack of exercise, overeating, drinking, smoking, various environmental pollutants, etc.

Fat, thrombus, plaque or the like may cause inflammation when they are accumulated on the inner wall of a blood vessel. As inflammatory substances are accumulated, the wall of the blood vessel becomes hard. If the blood vessel becomes narrow due to the accumulation of deposits on the wall of the blood vessel, the supply of blood and oxygen may be impaired and various vascular diseases may appear. Typical examples of vascular diseases include angina pectoris, myocardial infarction, cerebral stroke, and embolism of artery of lower extremity. Body paralysis or sudden death may occur unless a sufficient amount of blood and oxygen is supplied to the heart and the brain which are key organs for life support.

Cardiovascular diseases and cerebrovascular diseases are considered as major causes of death not only in Korea but also in other countries. These vascular diseases proceed silently. There is no special subjective symptom until the blood vessel is clogged to some extent or more. When ignored, the vascular diseases may be irrevocable. Therefore, even in the absence of subjective symptoms, it is important to diagnose and prevent cardiovascular diseases, cerebrovascular diseases and risk factors of atherosclerosis at an early stage.

Methods for diagnosing cardiovascular conditions and arteriosclerosis may be divided into an invasive method and a non-invasive method. Examples of the invasive method include angiography in which a blood vessel is imaged after injecting a contrast medium into the blood vessel, a method using a catheter, an intra-arterial micro ultrasound imaging method, and the like.

In addition, examples of the noninvasive method include an imaging diagnosis method using magnetic resonance imaging (MRI), computed tomography (CT), ultrasound or the like, a pulse wave velocity (PWV) measurement method, and a method of measuring an AI (Augmentation Index), which indicates a change in the magnitude of a pulse pressure, using a reflected wave. In recent years, the non-invasive method is widely used to diagnose the conditions of blood vessels.

A pulse wave is a graphical representation of a wavelength at which blood propagates in a wave form from the heart. A pulse wave transit time refers to the time taken for a pulse wave to travel between two arterial pulsation points. A pulse wave transit velocity can be obtained by dividing the length of a blood vessel between two pulse wave detection points by a propagation time difference. When an arterial blood vessel becomes hard, the pulse wave transit velocity increases. Thus, the pulse wave transit velocity is used as a quantitative index of arteriosclerosis.

The background art of the present invention is disclosed in Korean Patent Application Publication No. 10-2013-0095664 (published on Aug. 28, 2013).

SUMMARY

The present invention provides an apparatus for measuring blood circulation disorders using a pulse wave transit time, and a method therefor.

According to an embodiment of the present invention, there is provided an apparatus for measuring blood circulation disorders using a pulse wave transit time, including: a measurement unit configured to measure a pulse wave and an electrocardiogram of a subject to be measured; a detection unit configured to detect time information of a peak value point of the electrocardiogram and a peak value point and a foot value point of the pulse wave; an operation unit configured to calculate an average pulse wave transit time using the time information of the peak value point of the electrocardiogram and the peak value point and the foot value point of the pulse wave and calculate a blood circulation disorder determination index using the average pulse wave transit time; and a diagnosis unit configured to diagnose a blood circulation disorder using the blood circulation disorder determination index.

The measurement unit may be configured to measure a pulse wave of at least one of a carotid artery, a brachial artery, a radial artery and a femoral artery.

The operation unit may be configured to calculate a disease group/normal group determination index for determining a vascular disease, using an average pulse wave transit time between the peak value point of the electrocardiogram and the foot value point of the pulse wave.

The operation unit may be configured to calculate the disease group/normal group determination index using at least one of a value (EFf/EBf) obtained by dividing EFf by EBf, a value (EFf/ERf) obtained by dividing EFf by ERf, a value (CFf/CBf) obtained by dividing CFf by CBf and a value (CFf/CRf) obtained by dividing CFf by CRf, where the EFf is a parameter indicating an average pulse wave transit time between the peak value point of the electrocardiogram and the foot value point of the pulse wave measured at a femoral artery, the EBf is a parameter indicating an average pulse wave transit time between the peak value point of the electrocardiogram and the foot value point of the pulse wave measured at a brachial artery, the ERf is a parameter indicating an average pulse wave transit time between the peak value point of the electrocardiogram and the foot value point of the pulse wave measured at a radial artery, the CFf is a parameter indicating an average pulse wave transit time between the foot value points of the pulse waves measured at a carotid artery and a femoral artery, the CBf is a parameter indicating an average pulse wave transit time between the foot value points of the pulse waves measured at a carotid artery and a brachial artery, and the CRf is a parameter indicating an average pulse wave transit time between the foot value points of the pulse waves measured at a carotid artery and a radial artery.

The operation unit may be configured to calculate a cardiovascular disease group/cerebrovascular disease group determination index for determining a kind of a vascular disease, using an average pulse wave transit time between the peak value point of the electrocardiogram and the peak value point of the pulse wave.

The operation unit may be configured to calculate the cardiovascular disease group/cerebrovascular disease group determination index using at least one of a value (ECp/EFp) obtained by dividing ECp by EFp, a value (ECp/EBp) obtained by dividing ECp by EBp and a value (ECp/ERp) obtained by dividing ECp by ERp, where the EFp is a parameter indicating an average pulse wave transit time between the peak value point of the electrocardiogram and the peak value point of the pulse wave measured at a femoral artery, the EBp is a parameter indicating an average pulse wave transit time between the peak value point of the electrocardiogram and the peak value point of the pulse wave measured at a brachial artery, the ERp is a parameter indicating an average pulse wave transit time between the peak value point of the electrocardiogram and the peak value point of the pulse wave measured at a radial artery, and the ECp is a parameter indicating an average pulse wave transit time between the peak value point of the electrocardiogram and the peak value point of the pulse wave measured at a carotid artery.

According to another embodiment of the present invention, there is provided a method for measuring blood circulation disorders using a pulse wave transit time, including: a step of measuring a pulse wave and an electrocardiogram of a subject to be measured; a step of detecting time information of a peak value point of the electrocardiogram and a peak value point and a foot value point of the pulse wave; a step of calculating an average pulse wave transit time using the time information of the peak value point of the electrocardiogram and the peak value point and the foot value point of the pulse wave; a step of calculating a blood circulation disorder determination index using the average pulse wave transit time; and a step of diagnosing a blood circulation disorder using the blood circulation disorder determination index.

As described above, according to the present invention, it is possible to predict the risk of a vascular disease through the measurement of a pulse wave and an electrocardiogram (EKG). This makes it possible to measure blood circulation disorders in a noninvasive manner and at a low cost.

According to the present invention, a normal group and a cardio/cerebrovascular disease group can be primarily screened through the simple measurement of a pulse wave transit time. Furthermore, the present invention can be utilized in various fields such as a health checkup in hospitals and clinics, a wellness platform which is the current national interest, and other health management programs of individuals.

DETAILED DESCRIPTION

Hereinafter, embodiments of the present invention will be described in detail with reference to the accompanying drawings so that those skilled in the art can easily implement the present invention. However, the present invention may be embodied in many different forms and is not limited to the embodiments described here. In order to clearly explain the present invention, those parts unrelated to the present invention are omitted in the drawings. Similar parts are denoted by like reference numerals throughout the specification.

In the specification as a whole, when a certain part "includes" a certain component, it is meant that the part does not exclude other components but may further include other components unless specifically stated to the contrary.

Now, embodiments of the present invention will be described in detail with reference to the accompanying drawings so that those skilled in the art can easily implement the present invention.

Figure 1:
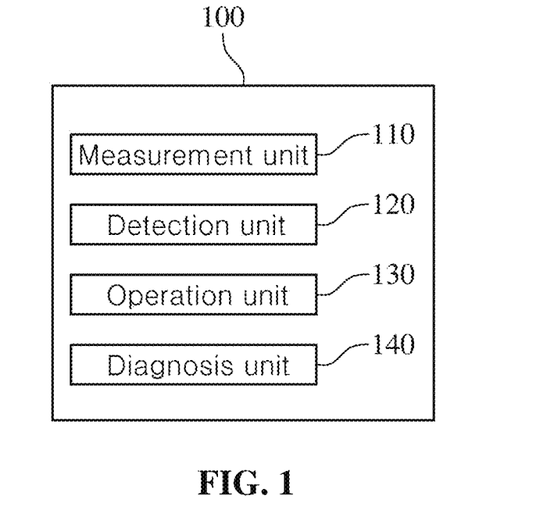
FIG. 1 is a configuration diagram showing a blood circulation disorder measurement apparatus according to an embodiment of the present disclosure.

First, the configuration of a blood circulation disorder measurement apparatus according to an embodiment of the present invention will be described with reference to FIG. 1. FIG. 1 is a diagram showing the configuration of a blood circulation disorder measurement apparatus.

As shown in FIG. 1, the blood circulation disorder measurement apparatus 100 according to an embodiment of the present invention includes a measurement unit 110, a detection unit 120, an operation unit 130 and a diagnosis unit 140.

First, the measurement unit 110 measures an electrocardiogram (EKG) and a pulse wave of a human body to be measured.

As used herein, the term "pulse wave" means a wave formed when the pulse is transmitted to a peripheral nerve. If there is arteriosclerosis, the shape of the pulse wave is changed and the propagation velocity of the pulse wave is increased. The measurement unit 110 may measure a pulse wave at the respective parts of the human body. In this case, the respective parts of the human body may include a carotid artery, a brachial artery, a radial artery and a femoral artery. The measurement unit 110 may include an IR or semiconductor type pulse wave signal acquisition sensor for measuring a pulse wave.

The term "electrocardiogram (EKG)" means a record of a change in electricity occurring locally due to the activity of the heart. The change in electricity may be recorded on the body surface because it is transmitted to the body surface via the tissue constituting a volumetric conductor. In the case of a human, an electric potential is induced and recorded by usually attaching an electrode to a specific part of the body surface. The measurement unit 110 measures an electrocardiogram of the human body. In this case, the measurement method of the electrocardiogram may include a derivation method in which an electrocardiogram is derived from both hands, a derivation method in which an electrocardiogram is derived from the right hand and the left foot, a derivation method in which an electrocardiogram is derived from the left hand and the left foot, and a derivation method using unipolar derivation. The derivation methods described above are well-known techniques that can be easily implemented by those skilled in the art. Thus, the detailed description thereof will be omitted.

The measurement unit 110 transmits the data of the electrocardiogram and the pulse wave measured from a measurement target person to the detection unit 120.

The detection unit 120 detects time information of a peak value point and a foot value point based on the data of the electrocardiogram and the pulse wave transmitted from the measurement unit 110.

The detection unit 120 detects time information of a peak value point and a foot value point from the measurement data of the pulse wave transmitted from the measurement unit 110 and detects time information of a peak value point from the measurement data of the electrocardiogram. In this case, the peak value point of the electrocardiogram refers to a point R in a QRS group of the electrocardiogram.

In this manner, the detection unit 120 detects the time information of the peak value point and the foot value point of the pulse wave and the time information of the peak value point of the electrocardiogram based the data transmitted from the measurement unit 110, and transmits the detected time information to the operation unit 130.

The operation unit 130 calculates an average value of a pulse wave transit time using the time information on the peak value point and the foot value point of the pulse wave and the peak value point of the electrocardiogram transmitted from the detection unit 120.

Hereinafter, parameters indicating the average value of the pulse wave transit time will be described with reference to Tables 1 and 2.

First, Table 1 is a table for explaining the parameters of the average value of the pulse wave transit time using the foot value point of the pulse wave according to an embodiment of the present invention.

TABLE 1

| Parameters | Meaning |
|---|---|
| EFf | Average pulse wave transit time between EKG R peak and femoral pulse wave foot |
| EBf | Average pulse wave transit time between EKG R peak and brachial pulse wave foot |
| ERf | Average pulse wave transit time between EKG R peak and radial pulse wave foot |
| CFf | Average pulse wave transit time between carotid and femoral pulse wave foot |
| CBf | Average pulse wave transit time between carotid and brachial pulse wave foot |
| CRf | Average pulse wave transit time between carotid and radial pulse wave foot |

As shown in Table 1, the parameters indicating the average value of the pulse wave transit time using the foot value point of the pulse wave includes EFf, EBf, ERf, CFf, CBf and CRf, and may further include other parameters.

In this regard, the average value of the pulse wave transit time obtained using the foot value point of the pulse wave refers to a value obtained by averaging the times between the foot values of the respective periods detected from the pulse wave.

As shown in Table 1, EFf is a parameter indicating the average pulse wave transit time between the peak value point of the electrocardiogram and the foot value point of the pulse wave measured at a femoral artery. EBf is a parameter indicating the average pulse wave transit time between the peak value point of the electrocardiogram and the foot value point of the pulse wave measured at a brachial artery.

ERf is a parameter indicating the average pulse wave transit time between the peak value point of the electrocardiogram and the foot value point of the pulse wave measured at a radial artery. CFf is a parameter indicating the average pulse wave transit time between the foot value points of the pulse wave measured at a carotid and a femoral artery.

CBf is a parameter indicating the average pulse wave transit time between the foot value points of the pulse wave measured at a carotid and a brachial artery. CRf is a parameter indicating the average pulse wave transit time between the foot value points of the pulse wave measured at a carotid and a radial artery.

Table 2 is a table for explaining the parameters of the average value of the pulse wave transit time using the peak value point of the pulse wave according to an embodiment of the present invention.

TABLE 2

| Parameters | Meaning |
|---|---|
| EFp | Average pulse wave transit time between EKG R peak and femoral pulse wave peak |
| EBp | Average pulse wave transit time between EKG R peak and brachial pulse wave peak |
| ERp | Average pulse wave transit time between EKG R peak and radial pulse wave peak |
| ECp | Average pulse wave transit time between EKG R peak and carotid pulse wave peak |

As shown in Table 2, the parameters indicating the average value of the pulse wave transit time using the peak value point of the pulse wave includes EFp, EBp, ERp and ECp, and may further include other parameters.

In this regard, the average value of the pulse wave transit time obtained using the peak value point of the pulse wave refers to a value obtained by averaging the times between the peak values of the respective periods detected from the pulse wave.

EFp is a parameter indicating the average pulse wave transit time between the peak value point of the electrocardiogram and the peak value point of the pulse wave measured at a femoral artery. EBp is a parameter indicating the average pulse wave transit time between the peak value point of the electrocardiogram and the peak value point of the pulse wave measured at a brachial artery.

ERp is a parameter indicating the average pulse wave transit time between the peak value point of the electrocardiogram and the peak value point of the pulse wave measured at a radial artery. ECp is a parameter indicating the average pulse wave transit time between the peak value point of the electrocardiogram and the peak value point of the pulse wave measured at a carotid.

Furthermore, the operation unit 130 may calculate a blood circulation disorder determination index using the parameters indicating the average pulse wave transit time. The blood circulation disorder determination index includes a disease group/normal group determination index and a cardiovascular disease group/cerebrovascular disease group determination index.

First, description will be made on the disease group/normal group determination index calculated using the parameters indicating the average pulse wave transit time, which are obtained by using the foot value point of the pulse wave.

The disease group/normal group determination index includes A1 to A11 and may further include other disease group/normal group determination index.

The disease group/normal group determination indices A1 to A4 are calculated using the parameters indicating the average pulse wave transit time, which are obtained by using the foot value point of the pulse wave.

The disease group/normal group determination index A1 indicates a value (EFf/EBf) obtained by dividing the parameter EFf by the parameter EBf. The disease group/normal group determination index A2 indicates a value (EFf/ERf) obtained by dividing the parameter EFf by the parameter ERf.

The disease group/normal group determination index A3 indicates a value (CFf/CBf) obtained by dividing the parameter CFf by the parameter CBf. The disease group/normal group determination index A4 indicates a value (CFf/CRf) obtained by dividing the parameter CFf by the parameter CRf.

The disease group/normal group determination indices A5 to A10 are calculated using the disease group/normal group determination indices A1 to A4.

The disease group/normal group determination index A5 is a determination index indicating the sum of two of the disease group/normal group determination indices A1 to A4 and may have a value of one of A1+A2, A1+A3, A1+A4, A2+A3, A2+A4 and A3+A4.

The disease group/normal group determination index A6 is a determination index indicating the sum of three of the disease group/normal group determination indices A1 to A4 and may have a value of one of A1+A2+A3, A1+A2+A4, A1+A3+A4 and A2+A3+A4.

The disease group/normal group determination index A7 is a determination index indicating the sum of the disease group/normal group determination indices A1 to A4 and may have a value of A1+A2+A3+A4.

The disease group/normal group determination index A8 is a determination index indicating the product of two of the disease group/normal group determination indices A1 to A4 and may have a value of one of A1*A2, A1*A3, A1*A4, A2*A3, A2*A4 and A3*A4.

The disease group/normal group determination index A9 is a determination index indicating the product of three of the disease group/normal group determination indices A1 to A4 and may have a value of one of A1*A2*A3, A1*A2*A4, A1*A3*A4 and A2*A3*A4.

The disease group/normal group determination index A10 is a determination index indicating the product of the disease group/normal group determination indices A1 to A4 and may have a value of A1*A2*A3*A4.

The disease group/normal group determination index A11 is a value indicating the sum of two of the values of the disease group/normal group determination index A8. Thus, the disease group/normal group determination index A11 may have a value of one of (A1*A2)+(A1*A3), (A1*A2)+(A1*A4), (A1*A2)+(A2*A3), (A1*A2)+(A2*A4), (A1*A2)+(A3*A4), (A1*A3)+(A1*A4), (A1*A3)+(A2*A3), (A1*A3)+(A2*A4), (A1*A3)+(A3*A4), (A1*A4)+(A2*A3), (A1*A4)+(A2*A4), (A1*A4)+(A3*A4), (A2*A3)+(A2*A4), (A2*A3)+(A3*A4) and (A2*A4)+(A3*A4).

Next, description will be made on a process in which the operation unit 130 calculates a cardiovascular disease group/cerebrovascular disease group determination index using the parameters indicating the average pulse wave transit time obtained using the peak value point of the pulse wave.

The cardiovascular disease group/cerebrovascular disease group determination index includes cardiovascular disease group/cerebrovascular disease group determination indices B1 to B8 and may further include other cardiovascular disease group/cerebrovascular disease group determination indices.

The cardiovascular disease group/cerebrovascular disease group determination indices B1 to B3 are calculated using the parameters indicating the average pulse wave transit time which is obtained using the peak value point of the pulse wave.

The cardiovascular disease group/cerebrovascular disease group determination index B1 indicates a value (ECp/EFp) obtained by dividing the parameter ECp by the parameter EFp. The cardiovascular disease group/cerebrovascular disease group determination index B2 indicates a value (ECp/EBp) obtained by dividing the parameter ECp by the parameter EBp.

The cardiovascular disease group/cerebrovascular disease group determination index B3 indicates a value (ECp/ERp) obtained by dividing the parameter ECp by the parameter ERp.

The cardiovascular disease group/cerebrovascular disease group determination indices B4 to B8 are calculated using the cardiovascular disease group/cerebrovascular disease group determination indices B1 to B3.

The cardiovascular disease group/cerebrovascular disease group determination index B4 is a determination index indicating the sum of two of the cardiovascular disease group/cerebrovascular disease group determination indices B1 to B3 and may have a value of one of B1+B2, B1+B3 and B2+B3.

The cardiovascular disease group/cerebrovascular disease group determination index B5 is a determination index indicating the sum of the cardiovascular disease group/cerebrovascular disease group determination indices B1 to B3 and may have a value of B1+B2+B3.

The cardiovascular disease group/cerebrovascular disease group determination index B6 is a determination index indicating the product of two of the cardiovascular disease group/cerebrovascular disease group determination indices B1 to B3 and may have a value of one of B1*B2, B1*B3 and B2*B3.

The cardiovascular disease group/cerebrovascular disease group determination index B7 is a determination index indicating the product of the cardiovascular disease group/cerebrovascular disease group determination indices B1 to B3 and may have a value of B1*B2*B3.

The cardiovascular disease group/cerebrovascular disease group determination index B8 is a determination index indicating the sum of two of the values of the cardiovascular disease group/cerebrovascular disease group determination index B6 and may have a value of one of (B1*B2)+(B1*B3), (B1*B2)+(B2*B3) and (B1*B3)+(B2*B3).

After calculating the disease group/normal group determination indices A1 to A11 and the cardiovascular disease group/cerebrovascular disease group determination indices B1 to B8 in this manner, the operation unit 130 transmits the calculated blood circulation disorder determination indices to the diagnosis unit 140. The calculated blood circulation disorder determination indices include the disease group/normal group determination indices A1 to A11 and the cardiovascular disease group/cerebrovascular disease group determination indices B1 to B8.

The diagnosis unit 140 diagnoses a blood circulation disorder using the blood circulation disorder determination indices transmitted from the operation unit 130. The diagnosis unit 140 may determine the existence of a vascular disease using the disease group/normal group determination indices A1 to A11 transmitted from the operation unit 130. Furthermore, the diagnosis unit 140 may determine whether the vascular disease is a cardiovascular disease or a cerebrovascular disease, using the cardiovascular disease group/cerebrovascular disease group determination indices B1 to B8 transmitted from the operation unit 130.

Figure 2A:
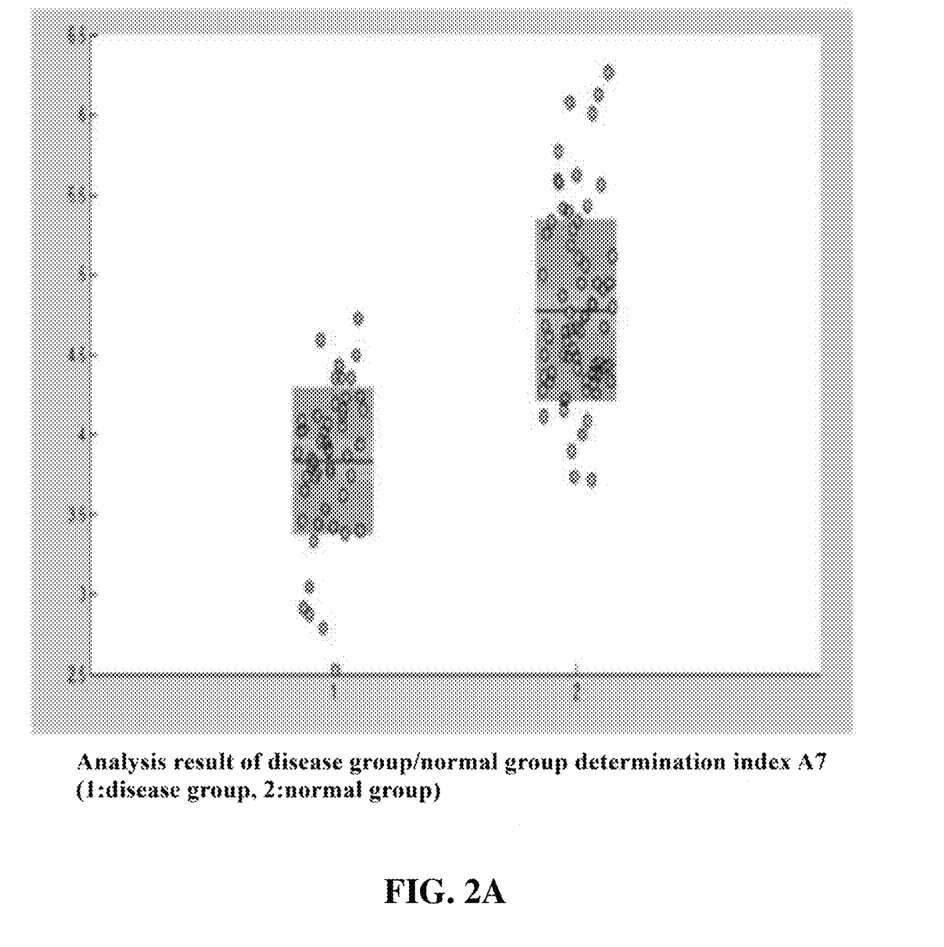
FIG. 2A is a graph showing an analysis result of a disease group/normal group determination index according to an embodiment of the present disclosure.
Figure 2B:
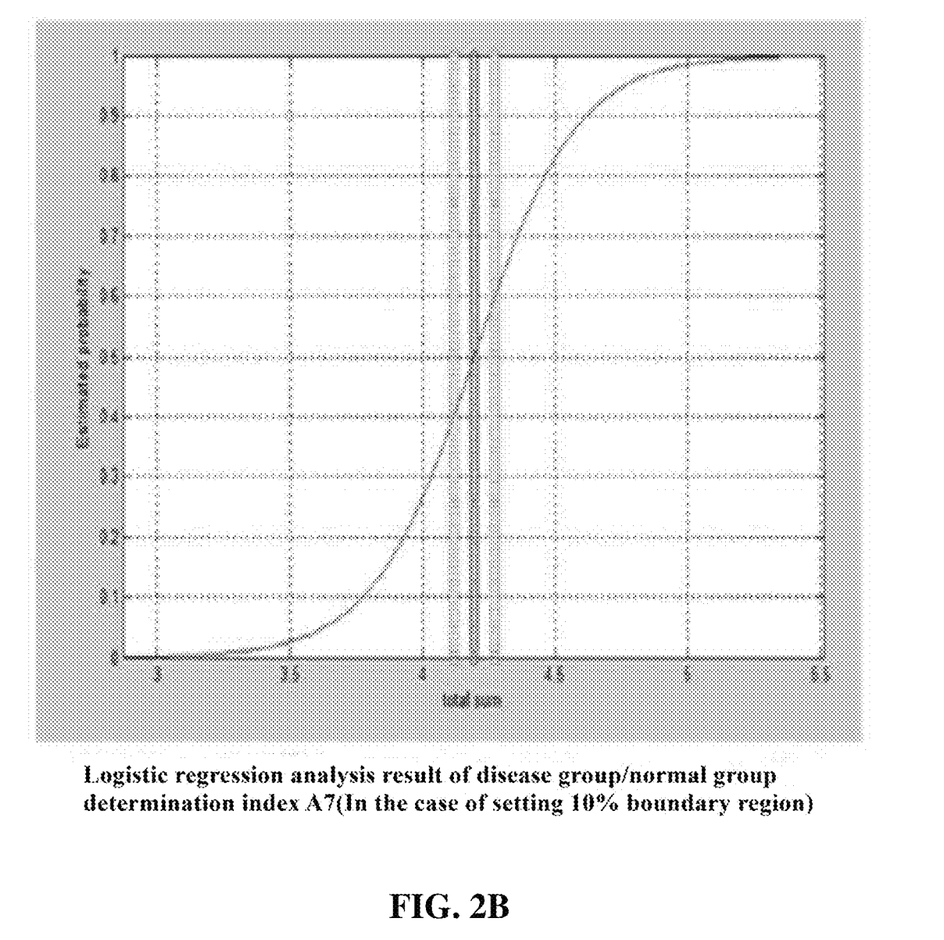
FIG. 2B is a graph showing a logistic regression analysis result of a disease group/normal group determination index according to an embodiment of the present disclosure.

Hereinafter, a vascular disease determination method according to an embodiment of the present invention will be described with reference to FIGS. 2A and 2B. FIGS. 2A and 2B show, by way of example, the analysis result of the disease group/normal group determination index A7.

Table 3 shows diagnosis criteria for determining a disease group and a normal group according to an embodiment of the present invention.

TABLE 3

| Determination index A7 | Diagnosis criteria |
| --- | --- |
| Normal group | More than 4.36 |
| Boundary region | 4.12 to 4.36 |
| Disease group | Less than 4.12 |

As shown in Table 3, the values of the determination index A7 in the boundary region are in a range of 4.12 to 4.36. If the value of the determination index A7 is more than 4.36, the subject falls within the normal group. If the value of the determination index A7 is less than 4.12, the subject falls within the disease group.

In this regard, the threshold value for determining the disease group and the normal group is an experimentally obtained value and may be changed depending on the result of a clinical test.

FIG. 2A is a graph showing the analysis result of the disease group/normal group determination index according to an embodiment of the present disclosure.

The analysis result of the disease group/normal group determination index reveals that in the case of vascular disease group 1, the values of the determination index A7 are concentrated and distributed around 3.75 smaller than 4.12 and further that in the case of normal group 2, the values of the determination index A7 are distributed around 4.75 larger than 4.36.

FIG. 2B is a graph showing the logistic regression analysis result of the disease group/normal group determination index according to an embodiment of the present disclosure.

In the logistic regression analysis, the sensitivity and the specificity of the vascular disease group and the normal group were calculated by setting the estimated probability so as to have boundary regions of predetermined percentages on the left and right sides on the basis of 50%. The estimated probability of 0 means the vascular disease group. The estimated probability of 1 means the normal group.

As a result of the logistic regression analysis, when the estimated probability is set so as to have boundary regions of 10% on the left side and 20% on the right side on the basis of 50%, the sensitivity and the specificity of the vascular disease group and the normal group were 90%.

Figure 3A:
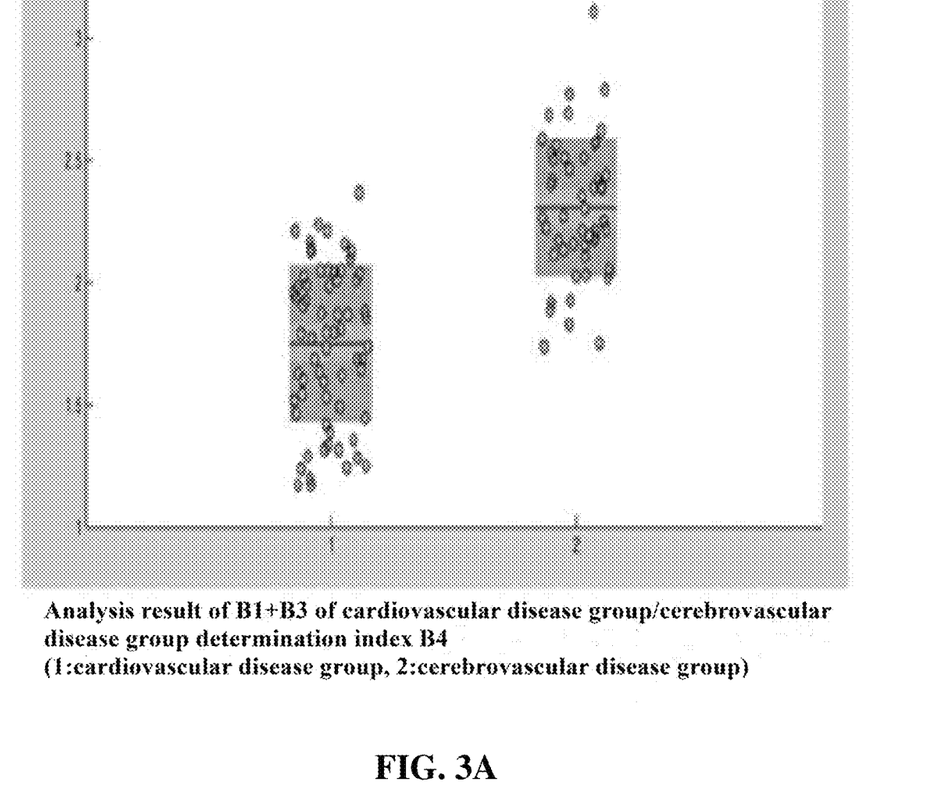
FIG. 3A is a graph showing an analysis result of a cardiovascular disease group/cerebrovascular disease group determination index according to an embodiment of the present disclosure.
Figure 3B:
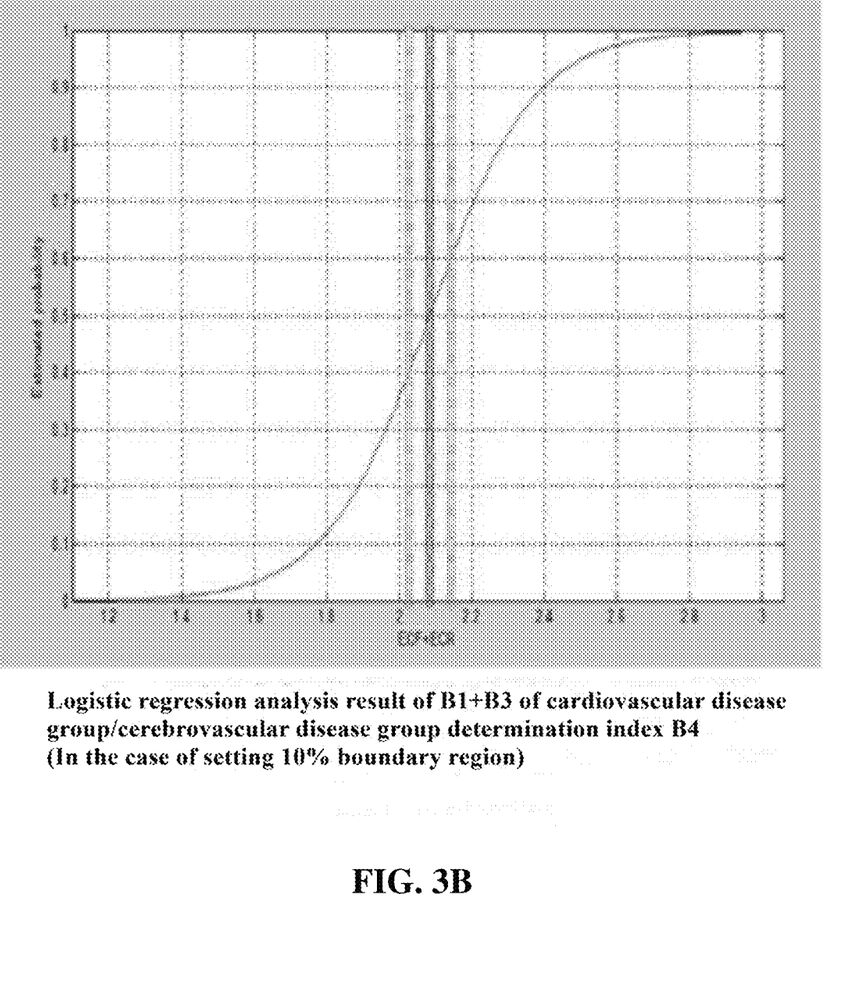
FIG. 3B is a graph showing a logistic regression analysis result of a cardiovascular disease group/cerebrovascular disease group determination index according to an embodiment of the present disclosure.

The determination of a cerebrovascular disease will be described with reference to FIGS. 3A and 3B. FIGS. 3A and 3B show, by way of example, the analysis results of the determination index for a value of B1+B3, i.e., a value of (ECp/EFp)+(ECp/ERp), of the cardiovascular disease group/cerebrovascular disease group determination index B4.

Table 4 shows the diagnosis criteria for determining a cardiovascular disease group and a cerebrovascular disease group according to an embodiment of the present invention.

TABLE 4

| Determination index B4-2 | Diagnosis criteria |
| --- | --- |
| Cerebrovascular disease | More than 2.17 |
| Boundary region | 1.89 to 2.17 |
| Cardiovascular disease | Less than 1.89 |

As shown in Table 4, the values of the determination index B4-2 (B1+B3, i.e., (ECp/EFp)+(ECp/ERp)) in the boundary region are in a range of 1.89 to 2.17. If the value of the determination index B4-2 is more than 2.17, the subject falls within the cerebrovascular disease group. If the value of the determination index B4-2 is less than 1.89, the subject falls within the cardiovascular disease group.

In this regard, the threshold value for determining the cardiovascular disease group and the cerebrovascular disease group is an experimentally obtained value and may be changed depending on the result of a clinical test.

FIG. 3A is a graph showing the analysis result of the cardiovascular disease group/cerebrovascular disease group determination index according to an embodiment of the present disclosure.

The analysis result of the cardiovascular disease group/cerebrovascular disease group determination index reveals that in the case of cardiovascular disease group 1, the values of the cardiovascular disease group/cerebrovascular disease group determination index B4-2 are concentrated and distributed around 1.75 smaller than 1.89 and further that in the case of cerebrovascular disease group 2, the values of the cardiovascular disease group/cerebrovascular disease group determination index B4-2 are distributed around 2.25 larger than 2.17.

FIG. 3B is a graph showing the logistic regression analysis result of the cardiovascular disease group/cerebrovascular disease group determination index according to an embodiment of the present disclosure.

In the logistic regression analysis, the sensitivity and the specificity of the cardiovascular disease group and the cerebrovascular disease group were calculated by setting the estimated probability so as to have boundary regions of predetermined percentages on the left and right sides on the basis of 50%. The estimated probability of 0 means the cardiovascular disease group. The estimated probability of 1 means the cerebrovascular disease group.

As a result of the logistic regression analysis, when the estimated probability is set so as to have boundary regions of 30% on the left side and 15% on the right side on the basis of 50%, the sensitivity and the specificity of the cardiovascular disease group and the cerebrovascular disease group were 90%.

Hereinafter, a blood circulation disorder measurement method according to an embodiment of the present invention will be described with reference to FIG. 4.

Figure 4:
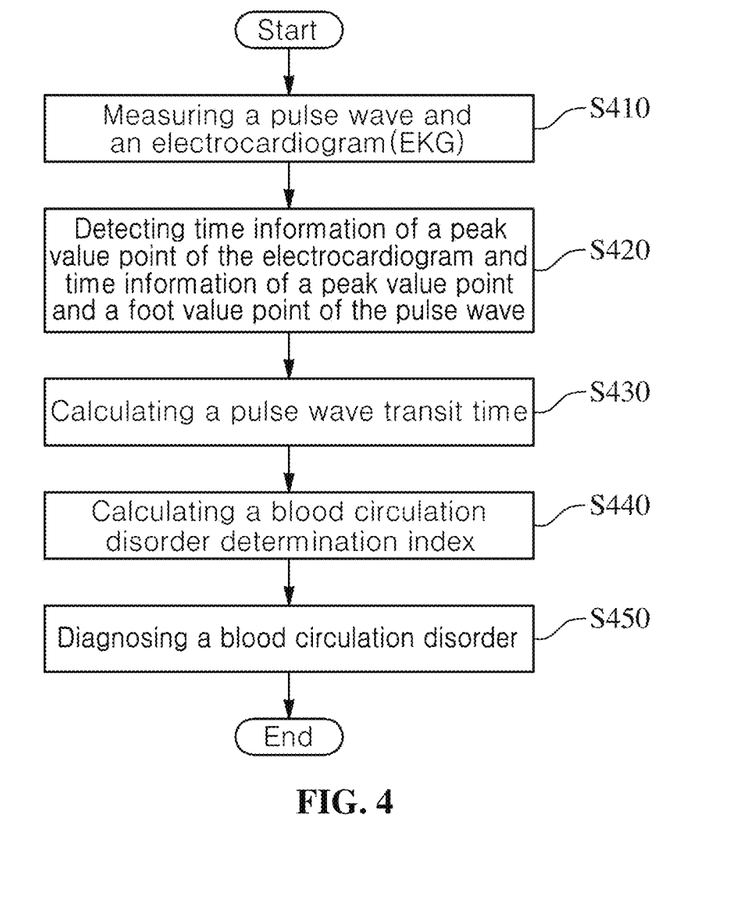
FIG. 4 is a flowchart showing a blood circulation disorder measurement method according to an embodiment of the present disclosure.

FIG. 4 is a flowchart showing a blood circulation disorder measurement method according to an embodiment of the present disclosure.

First, the measurement unit 110 measures an electrocardiogram and a pulse wave of a subject to be measured (S410).

The measurement unit 110 may measure a pulse wave at the respective parts of the human body. In this case, the respective parts of the human body may include a carotid artery, a brachial artery, a radial artery and a femoral artery. The measurement unit 110 may include an IR or semiconductor type pulse wave signal acquisition sensor for measuring a pulse wave. The measurement unit 110 transmits data of the measured electrocardiogram and data of the measured pulse wave to the detection unit 120.

The detection unit 120 detects time information for a peak value point of an electrocardiogram and a peak value point and a foot value point of a pulse wave using the electrocardiogram data and the pulse wave data transmitted from the measurement unit 110 (S420).

The detection unit 120 transmits the time information for the peak value point and the foot value point of the pulse wave and the time information for the peak value point of the electrocardiogram, i.e., the point R in a QRS group, to the operation unit 130.

The operation unit 130 calculates a pulse wave transit time using the time information for the peak value point of the electrocardiogram and the time information for the peak value point and the foot value point of the pulse wave transmitted from the detection unit 120 (S430).

The operation unit 130 may calculate parameters EFf, EBf, ERf, CFf, CBf and CRf indicating an average pulse wave transit time using the time information of the foot value point of the pulse wave. Furthermore, the operation unit 130 may calculate parameters EFp, EBp, ERp and ECp indicating an average pulse wave transit time using the time information of the peak value point of the pulse wave.

Since the process of acquiring the parameters indicating the average pulse wave transit time by the operation unit 130 has been described above, redundant description thereof will be omitted.

Next, the blood circulation disorder determination indices may be calculated using the parameters from which the average pulse wave transit time has been calculated using the time information of the peak value point and the foot value point of the pulse wave and the time information of the peak value point of the electrocardiogram (S440). The blood circulation disorder determination indices may include the disease group/normal group determination indices A1 to A11 and the cardiovascular disease group/cerebrovascular disease group determination indices B1 to B8.

The process of calculating the blood circulation disorder determination indices by the operation unit 130 has been described above. Thus, the redundant description thereof will be omitted.

The operation unit 130 calculates the blood circulation disorder determination indices in this way and transmits the blood circulation disorder determination indices to the diagnosis unit 140.

The diagnosis unit 140 determines a blood circulation disorder using the blood circulation disorder determination indices transmitted from the operation unit 130 (S450).

That is to say, the diagnosis unit 140 compares the calculated blood circulation disorder determination indices with a threshold value and determines whether the subject belongs to a vascular disease group or a normal group and whether the disease is a cardiovascular disease or a cerebrovascular disease.

According to the present invention described above, it is possible to predict the risk of a vascular disease through the measurement of a pulse wave and an electrocardiogram (EKG). This makes it possible to measure blood circulation disorders in a noninvasive manner and at a low cost.

According to the present invention, a normal group and a cardio/cerebrovascular disease group can be primarily screened through the simple measurement of a pulse wave transit time. Furthermore, the present invention can be utilized in various fields such as a health checkup in hospitals and clinics, a wellness platform which is the current national interest, and other health management programs of individuals.

While the present invention has been described with reference to the embodiments shown in the drawings, the aforementioned embodiments are nothing more than examples. Those skilled in the art will be able to appreciate that various modifications and other equivalent embodiments may be made from the aforementioned embodiments. Therefore, the true technical protection scope of the present invention should be determined by the technical idea of the appended claims.

What is claimed is:

1. An apparatus for diagnosing blood circulation disorders, the apparatus comprising:
   a measurement unit comprising an infrared or semiconductor pulse wave signal acquisition sensor and configured to measure signals including an electrocardiogram and pulse waves at various parts of a body of a subject to be diagnosed; and
   one or more processors configured to:
   detect time information of the signals measured by the measurement unit, wherein the time information includes at least one of a peak value point of the electrocardiogram, a peak value point of each of the pulse waves, and a foot value point of the each of the pulse waves;
   calculate average pulse wave transit times using the detected time information and calculate a blood circulation disorder determination indicator using the average pulse wave transit times; and
   diagnose a blood circulation disorder using the blood circulation disorder determination indicator,
   wherein the blood circulation disorder determination indicator includes a disease group/normal group determination indicator for determining a vascular disease,
   wherein the disease group/normal group determination indicator includes at least index A4, wherein:
   index A4 is calculated by dividing CFf by CRf,
   wherein the CFf is a parameter indicating an average pulse wave transit time between foot value points of pulse waves measured at a carotid artery and the femoral artery, and the CRf is a parameter indicating an average pulse wave transit time between the foot value points of the pulse waves measured at the carotid artery and the radial artery.

2. The apparatus of claim 1, wherein the disease group/normal group determination indicator further includes at least one of indices A1-A3 and A5-A11, wherein:
   index A1 is calculated by dividing EFf by EBf;
   index A2 is calculated by dividing EFf by ERf;
   index A3 is calculated by dividing CFf by CBf;
   index A5 is calculated by summing two of A1 to A4 (A1+A2, A1+A3, A1+A4, A2+A3, A2+A4, A3+A4);

index A6 is calculated by summing three of A1 to A4 (A1+A2+A3, A1+A2+A4, A1+A3+A4, A2+A3+A4);

index A7 is calculated by summing three of A1 to A4 (A1+A2+A3+A4);

index A8 is calculated by multiplying two of A1 to A4 (A1*A2, A1*A3, A1*A4, A2*A3, A2*A4, A3*A4);

index A9 is calculated by multiplying three of A1 to A4 (A1*A2*A3, A1*A2*A4, A1*A3*A4, A2*A3*A4);

index A10 is calculated by multiplying four of A1 to A4 (A1*A2*A3*A4); and index A11 is calculated by summing any two values obtained by multiplying two of A1 to A4 ((A1*A2)+(A1*A3), (A1*A2)+(A1*A4), (A1*A2)+(A2*A3), (A1*A2)+(A2*A4), (A1*A2)+(A3*A4), (A1*A3)+(A1*A4), (A1*A3)+(A2*A3), (A1*A3)+(A2*A4), (A1*A3)+(A3*A4), (A1*A4)+(A2*A3), (A1*A4)+(A2*A4), (A1*A4)+(A3*A4), (A2*A3)+(A2*A4), (A2*A3)+(A3*A4), (A2*A4)+(A3*A4)), and wherein the EFf is a parameter indicating an average pulse wave transit time between the peak value point of the electrocardiogram and a foot value point of a pulse wave measured at a femoral artery, the EBf is a parameter indicating an average pulse wave transit time between the peak value point of the electrocardiogram and a foot value point of a pulse wave measured at a brachial artery, the ERf is a parameter indicating an average pulse wave transit time between the peak value point of the electrocardiogram and a foot value point of a pulse wave measured at a radial artery, and the CBf is a parameter indicating an average pulse wave transit time between the foot value points of the pulse waves measured at the carotid artery and the brachial artery.

3. The apparatus of claim 1, wherein the blood circulation disorder determination indicator further includes a cardiovascular disease group/cerebrovascular disease group determination indicator for determining a kind of the vascular disease, and wherein the cardiovascular disease group/cerebrovascular disease group determination indicator is calculated using average pulse wave transit times between the peak value point of the electrocardiogram and the peak value point of the pulse waves.

4. The apparatus of claim 3, wherein the cardiovascular disease group/cerebrovascular disease group determination indicator is calculated using ECp, and wherein the ECp is a parameter indicating an average pulse wave transit time between the peak value point of the electrocardiogram and a peak value point of the pulse wave measured at the carotid artery.

5. The apparatus of claim 4, wherein the cardiovascular disease group/cerebrovascular disease group determination indicator includes indices B1-B3, wherein index B1 is calculated by dividing ECp by EFp, index B2 is calculated by dividing ECp by EBp, and index B3 is calculated by dividing ECp by ERp, and wherein the EFp is a parameter indicating an average pulse wave transit time between the peak value point of the electrocardiogram and a peak value point of the pulse wave measured at the femoral artery, the EBp is a parameter indicating an average pulse wave transit time between the peak value point of the electrocardiogram and a peak value point of the pulse wave measured at a brachial artery, and the ERp is a parameter indicating an average pulse wave transit time between the peak value point of the electrocardiogram and a peak value point of the pulse wave measured at a radial artery.

6. The apparatus of claim 5, wherein the cardiovascular disease group/cerebrovascular disease group determination indicator further includes indices B4-B8, wherein:

index B4 is calculated by summing any two of B1 to B3 (B1+B2, B1+B3, B2+B3);

index B5 is calculated by summing three of B1 to B3 (B1+B2+B3);

index B6 is calculated by multiplying any two of B1 to B3 (B1*B2, B1*B3, B2*B3);

index B7 is calculated by multiplying three of B1 to B3 (B1*B2*B3); and index B8 is calculated by summing any two values obtained by multiplying two of B1 to B3 ((B1*B2)+(B1*B3), (B1*B2)+(B2*B3), (B1*B3)+(B2*B3)).

7. A method for diagnosing blood circulation disorders, the method comprising:

measuring signals including an electrocardiogram and pulse waves at various parts of a body of a subject to be diagnosed using an infrared or semiconductor pulse wave signal acquisition sensor;

detecting time information of the measured signals, wherein the time information includes at least one of a peak value point of the electrocardiogram, a peak value point of each of the pulse waves, and a foot value point of the each of the pulse waves;

calculating average pulse wave transit times using the detected time information;

calculating a blood circulation disorder determination indicator using the average pulse wave transit times; and diagnosing a blood circulation disorder using the blood circulation disorder determination indicator, wherein the blood circulation disorder determination indicator includes a disease group/normal group determination indicator for determining a vascular disease, wherein the disease group/normal group determination indicator includes at least index A4, wherein:

index A4 is calculated by dividing CFf by CRf;

wherein the CFf is a parameter indicating an average pulse wave transit time between foot value points of pulse waves measured at a carotid artery and the femoral artery, and the CRf is a parameter indicating an average pulse wave transit time between the foot value points of the pulse waves measured at the carotid artery and the radial artery.

8. The method of claim 7, wherein the disease group/normal group determination indicator further includes at least one of indices A1-A3 and A5-A11, wherein:

index A1 is calculated by dividing EFf by EBf;

index A2 is calculated by dividing EFf by ERf;

index A3 is calculated by dividing CFf by CBf;

index A5 is calculated by summing two of A1 to A4 (A1+A2, A1+A3, A1+A4, A2+A3, A2+A4, A3+A4);

index A6 is calculated by summing three of A1 to A4 (A1+A2+A3, A1+A2+A4, A1+A3+A4, A2+A3+A4);

index A7 is calculated by summing three of A1 to A4 (A1+A2+A3+A4);

index A8 is calculated by multiplying two of A1 to A4 (A1*A2, A1*A3, A1*A4, A2*A3, A2*A4, A3*A4);

index A9 is calculated by multiplying three of A1 to A4 (A1*A2*A3, A1*A2*A4, A1*A3*A4, A2*A3*A4);

index A10 is calculated by multiplying four of A1 to A4 (A1*A2*A3*A4); and index A11 is calculated by summing any two values obtained by multiplying two of A1 to A4 ((A1*A2)+(A1*A3), (A1*A2)+(A1*A4), (A1*A2)+(A2*A3), (A1*A2)+(A2*A4), (A1*A2)+(A3*A4), (A1*A3)+

(A1*A4), (A1*A3)+(A2*A3), (A1*A3)+(A2*A4), (A1*A3)+(A3*A4), (A1*A4)+(A2*A3), (A1*A4)+(A2*A4), (A1*A4)+(A3*A4), (A2*A3)+(A2*A4), (A2*A3)+(A3*A4), (A2*A4)+(A3*A4)), and wherein the EFf is a parameter indicating an average pulse wave transit time between the peak value point of the electrocardiogram and a foot value point of a pulse wave measured at a femoral artery, the EBf is a parameter indicating an average pulse wave transit time between the peak value point of the electrocardiogram and a foot value point of a pulse wave measured at a brachial artery, the ERf is a parameter indicating an average pulse wave transit time between the peak value point of the electrocardiogram and a foot value point of a pulse wave measured at a radial artery, and the CBf is a parameter indicating an average pulse wave transit time between the foot value points of the pulse waves measured at the carotid artery and the brachial artery.

9. The method of claim 7, wherein the blood circulation disorder determination indicator further includes a cardiovascular disease group/cerebrovascular disease group determination indicator for determining a kind of the vascular disease using average pulse wave transit times between the peak value point of the electrocardiogram and the peak value point of the pulse waves.

10. The method of claim 9, wherein the cardiovascular disease group/cerebrovascular disease group determination indicator is calculated using ECp, and wherein the ECp is a parameter indicating an average pulse wave transit time between the peak value point of the electrocardiogram and a peak value point of the pulse wave measured at the carotid artery.

11. The method of claim 10, wherein the cardiovascular disease group/cerebrovascular disease group determination indicator includes at least one of indices B1-B3, wherein index B1 is calculated by dividing ECp by EFp, index B2 is calculated by dividing ECp by EBp, and index B3 is calculated by dividing ECp by ERp, and wherein the EFp is a parameter indicating an average pulse wave transit time between the peak value point of the electrocardiogram and a peak value point of the pulse wave measured at the femoral artery, the EBp is a parameter indicating an average pulse wave transit time between the peak value point of the electrocardiogram and a peak value point of the pulse wave measured at a brachial artery, and the ERp is a parameter indicating an average pulse wave transit time between the peak value point of the electrocardiogram and a peak value point of the pulse wave measured at a radial artery.

12. The method of claim 11, wherein the cardiovascular disease group/cerebrovascular disease group determination indicator further includes indices B4-B8, wherein:

index B4 is calculated by summing any two of B1 to B3 (B1+B2, B1+B3, B2+B3);

index B5 is calculated by summing three of B1 to B3 (B1+B2+B3);

index B6 is calculated by multiplying any two of B1 to B3 (B1*B2, B1*B3, B2*B3);

index B7 is calculated by multiplying three of B1 to B3 (B1*B2*B3); and index B8 is calculated by summing any two values obtained by multiplying two of B1 to B3 ((B1*B2)+(B1*B3), (B1*B2)+(B2*B3), (B1*B3)+(B2*B3)).

* * * * *